United States Patent
Ranucci et al.

(10) Patent No.: US 9,072,586 B2
(45) Date of Patent: Jul. 7, 2015

(54) IMPLANTABLE PROSTHESIS

(75) Inventors: Debra J. Ranucci, Warwick, RI (US); Tami L. Hamlin, Exeter, RI (US); Philip A. Tessier, Cranton, RI (US); Marianne Staudenmeier, North Kingstown, RI (US); Damian H. Tomlin, Kingston (JM)

(73) Assignee: C.R. Bard, Inc., Murray Hill, NJ (US)

( * ) Notice: Subject to any disclaimer, the term of this patent is extended or adjusted under 35 U.S.C. 154(b) by 1100 days.

(21) Appl. No.: 13/122,257

(22) PCT Filed: Oct. 2, 2009

(86) PCT No.: PCT/US2009/005424
§ 371 (c)(1),
(2), (4) Date: Aug. 16, 2011

(87) PCT Pub. No.: WO2010/039249
PCT Pub. Date: Apr. 8, 2010

(65) Prior Publication Data
US 2011/0288567 A1    Nov. 24, 2011

Related U.S. Application Data

(60) Provisional application No. 61/102,759, filed on Oct. 3, 2008.

(51) Int. Cl.
*A61F 2/24* (2006.01)
*A61F 2/00* (2006.01)
*A61B 19/00* (2006.01)

(52) U.S. Cl.
CPC ....... *A61F 2/0063* (2013.01); *A61B 2019/4884* (2013.01); *A61F 2250/0051* (2013.01)

(58) Field of Classification Search
CPC .... A61B 17/0057; A61B 17/12; A61F 2/063; A61F 2250/0051
USPC ............... 606/151; 623/23.72; 600/30
See application file for complete search history.

(56) References Cited

U.S. PATENT DOCUMENTS 2,621,145 A    12/1952    Sano
2,671,444 A    3/1954    Pease, Jr.
(Continued)

FOREIGN PATENT DOCUMENTS

CA    2114282    7/1994
DE    298 17 682 U1    4/1999
(Continued)

OTHER PUBLICATIONS

Brown, et al. "Comparison of prosthetic materials for abdominal wall reconstruction in the presence of contamination and infection", Annals of Surgery, pp. 705-711.
(Continued)

*Primary Examiner* — Gregory Anderson
*Assistant Examiner* — Christina Lauer
(74) *Attorney, Agent, or Firm* — Wolf, Greenfield & Sacks, P.C.

(57) ABSTRACT

An implantable prosthesis is provided for repairing an anatomical defect, such as a tissue or muscle defect, that promotes tissue of muscle ingrowth into the prosthesis and subsequently strengthens the area of the defect. The prosthesis is easy to manipulate and may be designed to minimize the incidence of postoperative adhesions between a portion of the prosthesis and surrounding tissue or organs. The prosthesis may include one or more layers of biologically compatible material that is suitable for repairing a defect. The prosthesis may include a support assembly to facilitate manipulation and deployment of the prosthesis. The support assembly may include a stiffening member that is surrounded by material that separates the stiffening member from the layer of material. The stiffening member may be located in a sleeve of material, such as mesh fabric. The stiffening member may be formed from a resorbable material.

44 Claims, 6 Drawing Sheets

(56) References Cited

U.S. PATENT DOCUMENTS

| | | |
|---|---|---|
| 3,054,406 A | 9/1962 | Usher |
| 3,124,136 A | 3/1964 | Usher |
| 3,272,204 A | 9/1966 | Artandi et al. |
| 3,625,209 A | 12/1971 | Clark |
| 3,874,388 A | 4/1975 | King et al. |
| 3,953,566 A | 4/1976 | Gore |
| 3,965,703 A | 6/1976 | Barnhardt |
| 4,000,348 A | 12/1976 | Harlow |
| 4,007,743 A | 2/1977 | Blake |
| 4,031,569 A | 6/1977 | Jacob |
| 4,051,848 A | 10/1977 | Levine |
| 4,147,824 A | 4/1979 | Dettmann et al. |
| 4,187,390 A | 2/1980 | Gore |
| 4,277,429 A | 7/1981 | Okita |
| 4,344,999 A | 8/1982 | Gohlke |
| 4,347,847 A | 9/1982 | Usher |
| 4,385,093 A | 5/1983 | Hubis |
| 4,400,833 A | 8/1983 | Kurland |
| 4,403,604 A | 9/1983 | Wilkinson et al. |
| 4,452,245 A | 6/1984 | Usher |
| 4,478,665 A | 10/1984 | Hubis |
| 4,482,516 A | 11/1984 | Bowman et al. |
| 4,561,434 A | 12/1985 | Taylor |
| 4,576,608 A | 3/1986 | Homsy |
| 4,585,458 A | 4/1986 | Kurland |
| 4,598,011 A | 7/1986 | Bowman |
| 4,633,873 A | 1/1987 | Dumican et al. |
| 4,655,221 A | 4/1987 | Devereux |
| 4,664,669 A | 5/1987 | Ohyabu et al. |
| 4,693,720 A | 9/1987 | Scharnberg et al. |
| 4,710,192 A | 12/1987 | Liotta et al. |
| 4,713,075 A | 12/1987 | Kurland |
| 4,725,279 A | 2/1988 | Woodroof |
| 4,760,102 A | 7/1988 | Moriyama et al. |
| 4,769,038 A | 9/1988 | Bendavid et al. |
| 4,784,899 A | 11/1988 | Ono et al. |
| 4,796,603 A | 1/1989 | Dahlke et al. |
| 4,816,339 A | 3/1989 | Tu et al. |
| 4,840,626 A | 6/1989 | Linsky et al. |
| 4,854,316 A | 8/1989 | Davis |
| 4,865,026 A | 9/1989 | Barrett |
| 4,871,365 A | 10/1989 | Dumican |
| 4,882,162 A | 11/1989 | Ikada et al. |
| 4,900,629 A | 2/1990 | Pitolaj |
| 4,902,423 A | 2/1990 | Bacino |
| 4,917,089 A | 4/1990 | Sideris |
| 4,923,464 A | 5/1990 | DiPisa, Jr. |
| 4,942,875 A | 7/1990 | Hlavacek et al. |
| 4,955,907 A | 9/1990 | Ledergerber |
| 4,994,084 A | 2/1991 | Brennan |
| 4,997,440 A | 3/1991 | Dumican |
| 5,002,551 A | 3/1991 | Linsky et al. |
| 5,006,106 A | 4/1991 | Angelchik |
| 5,007,916 A | 4/1991 | Linsky et al. |
| 5,032,445 A | 7/1991 | Scantlebury et al. |
| 5,092,884 A | 3/1992 | Devereux et al. |
| 5,098,779 A | 3/1992 | Kranzler et al. |
| 5,100,422 A | 3/1992 | Berguer et al. |
| 5,104,400 A | 4/1992 | Berguer et al. |
| 5,108,420 A | 4/1992 | Marks |
| 5,110,527 A | 5/1992 | Harada et al. |
| 5,116,357 A | 5/1992 | Eberbach |
| 5,116,360 A | 5/1992 | Pinchuk et al. |
| 5,122,155 A | 6/1992 | Eberbach |
| 5,141,515 A | 8/1992 | Eberbach |
| 5,141,522 A | 8/1992 | Landi |
| 5,147,384 A | 9/1992 | LaRocca |
| 5,147,401 A | 9/1992 | Bakker et al. |
| 5,171,259 A | 12/1992 | Inoue |
| 5,192,301 A | 3/1993 | Kamiya et al. |
| 5,195,542 A | 3/1993 | Gazielly et al. |
| 5,217,494 A | 6/1993 | Coggins et al. |
| 5,217,797 A | 6/1993 | Knox et al. |
| 5,222,987 A | 6/1993 | Jones |
| 5,234,739 A | 8/1993 | Tanaru et al. |
| 5,234,751 A | 8/1993 | Harada et al. |
| 5,254,133 A | 10/1993 | Seid |
| 5,258,000 A | 11/1993 | Gianturco |
| 5,282,851 A | 2/1994 | Jacob-LaBarre |
| 5,282,856 A | 2/1994 | Ledergerber |
| 5,290,217 A | 3/1994 | Campos |
| 5,292,328 A | 3/1994 | Hain et al. |
| 5,326,355 A | 7/1994 | Landi |
| 5,333,624 A | 8/1994 | Tovey |
| 5,334,217 A | 8/1994 | Das |
| 5,350,399 A | 9/1994 | Erlebacher et al. |
| 5,356,432 A | 10/1994 | Rutkow et al. |
| 5,358,678 A | 10/1994 | Nakamura et al. |
| 5,366,460 A | 11/1994 | Eberbach |
| 5,368,602 A | 11/1994 | de la Torre |
| 5,370,650 A | 12/1994 | Tovey et al. |
| 5,397,331 A | 3/1995 | Himpens et al. |
| 5,405,360 A | 4/1995 | Tovey |
| 5,411,550 A | 5/1995 | Herweck et al. |
| 5,413,597 A | 5/1995 | Krajicek |
| 5,425,740 A | 6/1995 | Hutchinson, Jr. |
| 5,425,744 A | 6/1995 | Fagan et al. |
| 5,433,996 A | 7/1995 | Kranzler et al. |
| 5,451,235 A | 9/1995 | Lock et al. |
| 5,456,720 A | 10/1995 | Schultz et al. |
| 5,458,636 A | 10/1995 | Brancato |
| 5,461,885 A | 10/1995 | Yokoyama et al. |
| 5,480,436 A | 1/1996 | Bakker et al. |
| 5,504,170 A | 4/1996 | Wu |
| 5,505,887 A | 4/1996 | Zdrahala et al. |
| 5,507,811 A | 4/1996 | Koike et al. |
| 5,508,036 A | 4/1996 | Bakker et al. |
| 5,512,624 A | 4/1996 | Howard, Jr. et al. |
| 5,514,231 A | 5/1996 | Thomas |
| 5,514,633 A | 5/1996 | Noguchi et al. |
| 5,519,004 A | 5/1996 | Urry |
| 5,522,896 A | 6/1996 | Prescott |
| 5,531,759 A | 7/1996 | Kensey et al. |
| 5,545,178 A | 8/1996 | Kensey et al. |
| 5,552,100 A | 9/1996 | Shannon et al. |
| 5,569,273 A | 10/1996 | Titone et al. |
| 5,591,234 A | 1/1997 | Kirsch |
| 5,593,441 A | 1/1997 | Lichtenstein et al. |
| 5,599,606 A | 2/1997 | Disselbeck et al. |
| 5,601,579 A | 2/1997 | Semertzides |
| 5,614,284 A | 3/1997 | Kranzler et al. |
| 5,634,931 A | 6/1997 | Kugel |
| 5,634,944 A | 6/1997 | Magram |
| 5,641,443 A | 6/1997 | Calcote et al. |
| 5,641,571 A | 6/1997 | Mayer et al. |
| 5,645,915 A | 7/1997 | Kranzler et al. |
| 5,653,755 A | 8/1997 | Ledergerber |
| 5,653,760 A | 8/1997 | Saffran |
| 5,677,031 A | 10/1997 | Allan et al. |
| 5,677,047 A | 10/1997 | Thomas |
| 5,686,033 A | 11/1997 | Shimizu |
| 5,686,090 A * | 11/1997 | Schilder et al. ............... 424/423 |
| 5,688,836 A | 11/1997 | Yamamoto et al. |
| 5,690,878 A | 11/1997 | Tuminello et al. |
| 5,695,525 A | 12/1997 | Mulhauser et al. |
| 5,697,390 A | 12/1997 | Garrison et al. |
| 5,697,978 A | 12/1997 | Sgro |
| 5,698,300 A | 12/1997 | Wimmer et al. |
| 5,702,416 A | 12/1997 | Kieturakis et al. |
| 5,708,044 A | 1/1998 | Branca |
| 5,709,707 A | 1/1998 | Lock et al. |
| 5,713,842 A | 2/1998 | Kay |
| 5,716,408 A | 2/1998 | Eldridge et al. |
| 5,716,409 A | 2/1998 | Debbas |
| 5,721,023 A | 2/1998 | Ostapchenko |
| 5,722,992 A | 3/1998 | Goldmann |
| 5,725,577 A | 3/1998 | Saxon |
| 5,733,337 A | 3/1998 | Carr, Jr. et al. |
| 5,741,297 A | 4/1998 | Simon |
| 5,743,917 A | 4/1998 | Saxon |
| 5,759,204 A | 6/1998 | Seare, Jr. |
| 5,766,246 A | 6/1998 | Mulhauser et al. |
| 5,769,864 A | 6/1998 | Kugel |
| 5,788,626 A | 8/1998 | Thompson |

(56) References Cited

U.S. PATENT DOCUMENTS

| | | | |
|---|---|---|---|
| 5,795,584 | A | 8/1998 | Totakura et al. |
| 5,813,975 | A | 9/1998 | Valenti |
| 5,824,082 | A | 10/1998 | Brown |
| 5,836,961 | A | 11/1998 | Kieturakis et al. |
| 5,855,613 | A | 1/1999 | Antanavich et al. |
| 5,861,034 | A | 1/1999 | Taira et al. |
| 5,871,498 | A | 2/1999 | Jervis et al. |
| 5,879,366 | A | 3/1999 | Shaw et al. |
| 5,916,225 | A | 6/1999 | Kugel |
| 5,919,232 | A | 7/1999 | Chaffringeon et al. |
| 5,919,233 | A | 7/1999 | Knopf et al. |
| 5,922,026 | A | 7/1999 | Chin |
| 5,948,020 | A | 9/1999 | Yoon et al. |
| 5,954,767 | A | 9/1999 | Pajotin et al. |
| 5,965,074 | A | 10/1999 | Aubertin et al. |
| 5,972,007 | A | 10/1999 | Sheffield et al. |
| 5,972,008 | A | 10/1999 | Kalinski et al. |
| D416,327 | S | 11/1999 | Kugel |
| 5,990,378 | A | 11/1999 | Ellis |
| 5,990,380 | A | 11/1999 | Marotta et al. |
| 6,004,333 | A | 12/1999 | Sheffield et al. |
| 6,025,044 | A | 2/2000 | Campbell et al. |
| 6,030,694 | A | 2/2000 | Dolan et al. |
| 6,031,148 | A | 2/2000 | Hayes et al. |
| 6,036,724 | A | 3/2000 | Lentz et al. |
| 6,048,484 | A | 4/2000 | House et al. |
| 6,066,776 | A | 5/2000 | Goodwin et al. |
| 6,077,281 | A | 6/2000 | Das |
| 6,080,182 | A | 6/2000 | Shaw et al. |
| 6,080,198 | A | 6/2000 | Lentz et al. |
| 6,080,472 | A | 6/2000 | Huang et al. |
| 6,090,116 | A | 7/2000 | D'Aversa et al. |
| 6,099,791 | A | 8/2000 | Shannon et al. |
| 6,113,641 | A | 9/2000 | Leroy et al. |
| 6,120,539 | A | 9/2000 | Eldridge et al. |
| 6,133,165 | A | 10/2000 | Tamaru et al. |
| 6,162,537 | A | 12/2000 | Martin et al. |
| 6,162,962 | A | 12/2000 | Hinsch et al. |
| 6,168,739 | B1 | 1/2001 | Moeder |
| 6,171,318 | B1 | 1/2001 | Kugel et al. |
| 6,174,320 | B1 | 1/2001 | Kugel et al. |
| 6,176,863 | B1 | 1/2001 | Kugel et al. |
| 6,176,875 | B1 | 1/2001 | Lenker et al. |
| 6,177,533 | B1 | 1/2001 | Woodward |
| 6,187,043 | B1 | 2/2001 | Ledergerber |
| 6,192,944 | B1 | 2/2001 | Greenhalgh |
| 6,193,731 | B1 | 2/2001 | Oppelt et al. |
| 6,210,439 | B1 | 4/2001 | Firmin et al. |
| 6,214,020 | B1 | 4/2001 | Mulhauser et al. |
| 6,214,029 | B1 | 4/2001 | Thill et al. |
| 6,218,000 | B1 | 4/2001 | Rudolf et al. |
| 6,224,616 | B1 | 5/2001 | Kugel |
| 6,235,377 | B1 | 5/2001 | Dillon et al. |
| 6,241,768 | B1 | 6/2001 | Agarwal et al. |
| 6,258,124 | B1 | 7/2001 | Darois et al. |
| 6,262,209 | B1 | 7/2001 | Kapeliouchko et al. |
| 6,262,332 | B1 | 7/2001 | Ketharanathan |
| 6,267,772 | B1 | 7/2001 | Mulhauser et al. |
| 6,270,530 | B1 | 8/2001 | Eldridge et al. |
| 6,274,043 | B1 | 8/2001 | Newman et al. |
| 6,280,453 | B1 | 8/2001 | Kugel et al. |
| 6,287,316 | B1 | 9/2001 | Agarwal et al. |
| 6,287,337 | B1 | 9/2001 | Martakos et al. |
| 6,287,497 | B1 | 9/2001 | Kawachi et al. |
| 6,290,708 | B1 | 9/2001 | Kugel et al. |
| 6,309,343 | B1 | 10/2001 | Lentz et al. |
| 6,315,791 | B1 | 11/2001 | Gingras et al. |
| 6,497,650 | B1 | 12/2002 | Nicolo |
| 6,551,356 | B2 | 4/2003 | Rousseau |
| 6,575,988 | B2 | 6/2003 | Rousseau |
| 6,652,595 | B1 | 11/2003 | Nicolo |
| 6,669,735 | B1 | 12/2003 | Pelissier |
| 6,790,213 | B2 | 9/2004 | Cherok et al. |
| 6,800,082 | B2 | 10/2004 | Rousseau |
| 6,926,723 | B1 | 8/2005 | Mulhauser et al. |
| 6,991,637 | B2 | 1/2006 | Crawley et al. |
| 7,101,381 | B2 | 9/2006 | Ford et al. |
| 7,513,865 | B2 | 4/2009 | Bourne et al. |
| 7,544,213 | B2 | 6/2009 | Adams |
| 7,824,420 | B2 | 11/2010 | Eldridge et al. |
| 2002/0103494 | A1 | 8/2002 | Pacey |
| 2003/0078602 | A1* | 4/2003 | Rousseau .................. 606/151 |
| 2004/0078077 | A1* | 4/2004 | Binette et al. ............ 623/13.17 |
| 2004/0215219 | A1 | 10/2004 | Eldridge et al. |
| 2005/0149080 | A1 | 7/2005 | Hunter et al. |
| 2006/0025785 | A1 | 2/2006 | Cully et al. |
| 2006/0064175 | A1* | 3/2006 | Pelissier et al. ........... 623/23.72 |
| 2008/0147200 | A1 | 6/2008 | Rousseau et al. |
| 2009/0082792 | A1 | 3/2009 | Koyfman et al. |
| 2009/0270999 | A1 | 10/2009 | Brown |

FOREIGN PATENT DOCUMENTS

| | | |
|---|---|---|
| EP | 0194192 A1 | 9/1986 |
| EP | 0334046 A2 | 9/1989 |
| EP | 0358819 A1 | 3/1990 |
| EP | 0362113 A1 | 4/1990 |
| EP | 0474887 A1 | 3/1992 |
| EP | 0719527 A1 | 7/1996 |
| EP | 0827724 A2 | 3/1998 |
| FR | 2744906 A1 | 8/1997 |
| GB | 1 352 282 | 5/1974 |
| GB | 1 406 271 | 9/1975 |
| JP | 2001-506906 | 5/2001 |
| JP | 2005-514156 | 5/2005 |
| SU | 676285 | 7/1979 |
| SU | 782814 | 11/1980 |
| SU | 1718857 | 3/1992 |
| WO | WO 82/04390 A1 | 12/1982 |
| WO | WO 88/01853 A1 | 3/1988 |
| WO | WO 90/14796 A1 | 12/1990 |
| WO | WO 92/10218 A1 | 6/1992 |
| WO | WO 92/19162 A2 | 11/1992 |
| WO | WO 93/17635 A1 | 9/1993 |
| WO | WO 94/17747 A1 | 8/1994 |
| WO | WO 96/09795 A1 | 4/1996 |
| WO | WO 96/14805 A1 | 5/1996 |
| WO | WO 97/21461 A1 | 6/1997 |
| WO | WO 97/22310 A1 | 6/1997 |
| WO | WO 97/35533 A1 | 10/1997 |
| WO | WO 98/14134 A2 | 4/1998 |
| WO | WO 00/07520 A1 | 2/2000 |
| WO | WO 01/08594 A1 | 2/2001 |
| WO | WO 02/22047 A1 | 3/2002 |

OTHER PUBLICATIONS

Cardona, "Prosthokreatoplasty" from Cornea, 1983 pp. 179-184.

Grant, A.M., "Open Mesh Versus Non-Mesh Repair of Groin Hernia Meta-Analysis of Randomized Trials Leased on Individual Patient Data," Hernia, 2002, vol. 6, pp. 130-136.

International Search Report and Written Opinion of the International Searching Authority for International application No. PCT/US2009/005424, dated Feb. 4, 2010.

Jenkins, et al. "A comparison of prosthetic materials used to repair abdominal wall defects" Surgery, Aug. 1983, pp. 392-398.

Johnson & Johnson "Prevention of postsurgical adhesions by Interceed (TC7), an absorbable adhesion barrier . . . " Fertility and Sterility, Jun. 6, 1989 pp. 933-938.

Uzzo, et al. "The Effects of mesh bioprosthesis on the spermatic cord structures: A preliminary report in a canine model" The Journal of Urology, Apr. 1999, pp. 1344-1349.

Walker, et al. "Double-Layer Prostheses for Repair of Abdominal Wall Defects in a Rabbit Model", Journal of Surgical Research, Jul. 1, 1993, pp. 32-37.

English translation of the Notice of Reasons for Rejection, mailed Aug. 30, 2013, for Japanese Patent Application No. 2011-530052 (5 pages).

* cited by examiner

IMPLANTABLE PROSTHESIS

CROSS-REFERENCE TO RELATED APPLICATIONS

This application is a national stage filing under 35 U.S.C. §371 of International Application No. PCT/US2009/005424, filed Oct. 2, 2009, which claims the benefit of U.S. Provisional Patent Application No. 61/102,759, filed Oct. 3, 2008. These applications are incorporated by reference in their entirety.

FIELD OF INVENTION

The present invention relates to an implantable prosthesis and, more particularly, to a prosthesis for soft tissue or muscle defects.

DISCUSSION OF RELATED ART

Various prosthetic materials are used to repair and/or reinforce anatomical defects, such as tissue and muscle wall hernias. For example, ventral and inguinal hernias are commonly repaired using a sheet of biocompatible fabric, such as a knitted polypropylene mesh (BARD MESH). Tissue integration with the fabric, such as by tissue ingrowth into the fabric, eventually completes the repair.

In certain procedures, the prosthetic fabric may come into contact with tissue or organs potentially leading to undesirable postoperative adhesions and undesirable tissue attachment between the mesh and the tissue or organs. To avoid such adhesions, a prosthesis may be covered with an adhesion resistant barrier. Examples of such prostheses are described in U.S. Pat. Nos. 5,593,441; 5,725,577 and 6,120,539, each of which is assigned to C. R. Bard, Inc.

For some procedures, a prosthesis may be provided with a support member to facilitate placement and/or support of the prosthetic fabric at a defect site. Examples of various configurations of such prostheses are described in U.S. Pat. Nos. 5,634,931; 5,695,525; 6,669,735 and 6,790,213, each of which is also assigned to C. R. Bard, Inc.

SUMMARY OF THE INVENTION

The present invention relates to an implantable prosthesis for repairing an anatomical defect, such as a tissue or muscle wall defect.

In one embodiment, an implantable prosthesis comprises a first layer of material, and a support assembly attached to the layer of material. The support assembly includes a stiffening member and a sleeve of material surrounding the stiffening member.

In another embodiment, an implantable prosthesis comprises a first layer of mesh, a second layer of mesh attached to the first layer of mesh with at least one pocket therebetween, and a support assembly located between the first and second mesh layers. The support assembly includes a stiffening member that is surrounded by material located between the stiffening member and the first and second layers of mesh.

In a further embodiment, an implantable prosthesis comprises a first layer of mesh fabric, a second layer of mesh fabric attached to the first layer of mesh fabric with at least one pocket therebetween, a support assembly located between the first and second layers of mesh fabric, and a barrier layer that inhibits the formation of adhesions thereto. The barrier layer is attached to at least one of the first layer, the second layer and the support assembly. The support assembly includes a resorbable stiffening member surrounded with a sleeve of mesh fabric.

Various embodiments of the present invention provide certain advantages and overcome certain drawbacks of prior prostheses. Embodiments of the invention may not share the same advantages, and those that do may not share them under all circumstances. This being said, the present invention provides numerous advantages including ease of implantation and promotion of desired tissue or muscle growth.

BRIEF DESCRIPTION OF THE DRAWINGS

Various embodiments of the invention will now be described, by way of example, with reference to the accompanying drawings, in which.

DESCRIPTION OF ILLUSTRATIVE EMBODIMENTS

An implantable prosthesis is provided for repairing an anatomical defect, such as a tissue or muscle defect, that promotes tissue of muscle ingrowth into the prosthesis and subsequently strengthens the area of the defect. The prosthesis is easy to manipulate and may be designed to minimize the incidence of postoperative adhesions between a portion of the prosthesis and surrounding tissue or organs. In addition, the prosthesis strikes a balance between being sufficiently rigid to aid in manipulation and deployment in the area of desired coverage and sufficiently flexible to be acceptable to both the surgeon and the patient. Further, the prosthesis may be constructed to allow it to be provisionally held in place at desired locations until sufficient tissue ingrowth occurs.

Embodiments of the prosthesis may be particularly suited for the repair of various soft tissue or muscle wall defects, including, but not limited to, inguinal and ventral hernias, chest or abdominal wall reconstruction or large defects, such as those that may occur in obese patients. The prosthesis may include one or more features, each independently or in combination, contributing to such attributes.

The prosthesis may include one or more layers of biologically compatible material that is suitable for repairing a defect. The prosthesis may include a support assembly that is attached to or integrated with the layer of material to facilitate manipulation and deployment of the prosthesis. The support assembly may include a stiffening member that is surrounded by material that separates the stiffening member from the layer of material. The stiffening member may be located in a sleeve of material. The stiffening member may be formed from a resorbable material. The sleeve may include interstices or openings that allow tissue or muscle ingrowth and/or facilitate resorption of the stiffening member.

Figure 1:
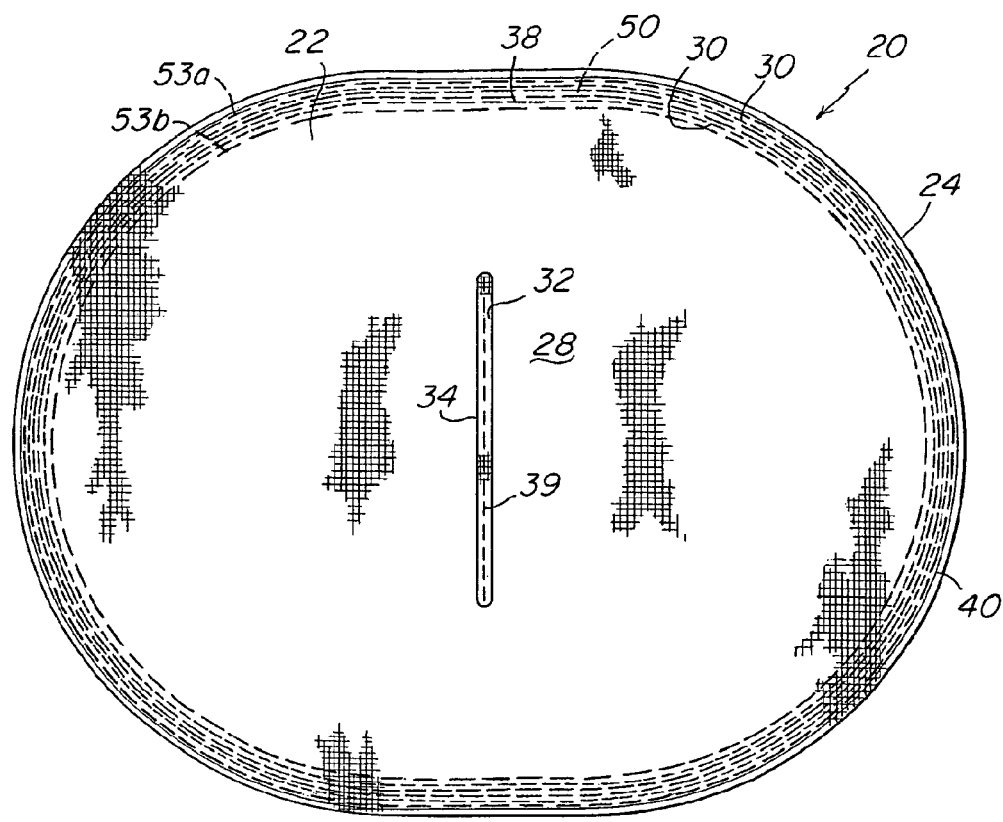
FIG. 1 is a top plan view of an implantable prosthesis according to one illustrative embodiment of the present invention.
Figure 2:
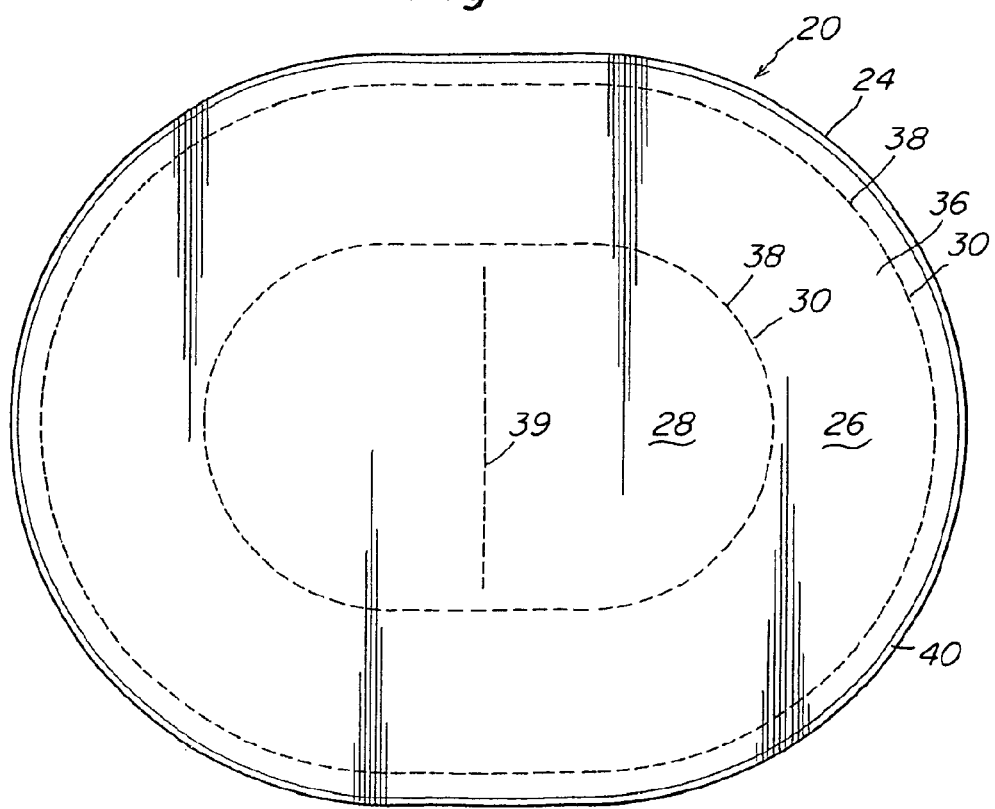
FIG. 2 is a bottom plan view of the prosthesis of FIG. 1.
Figure 3:
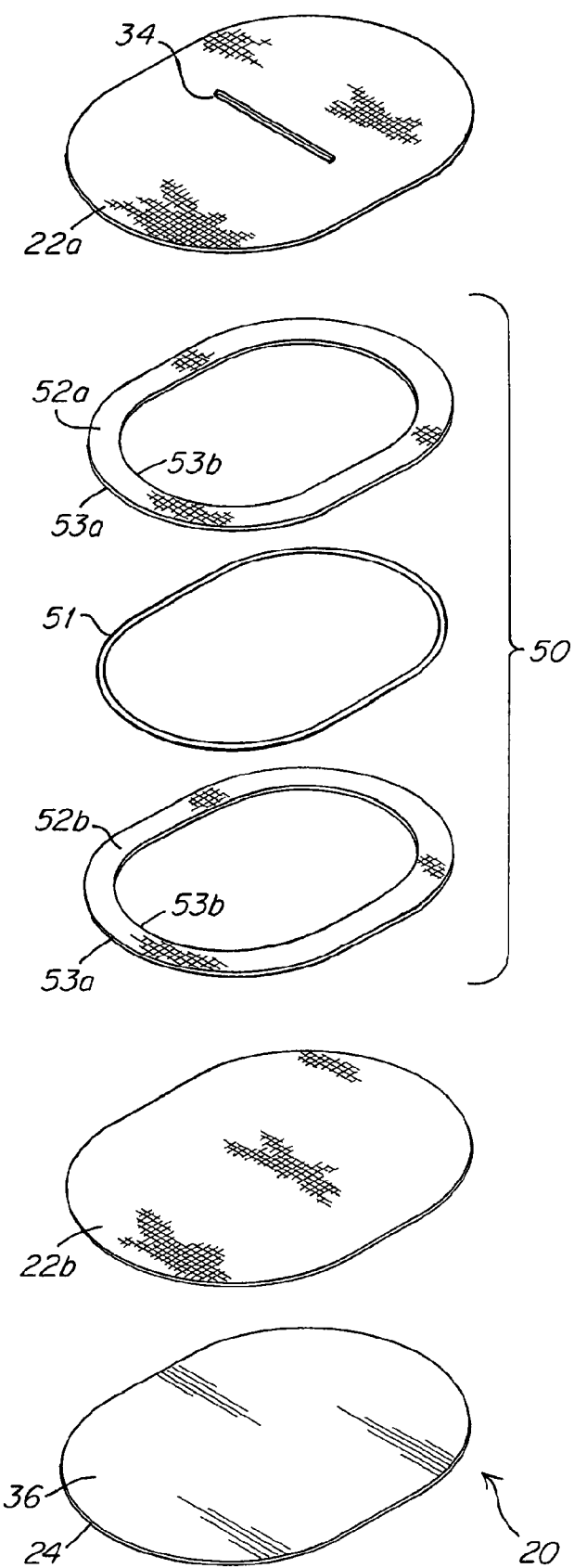
FIG. 3 is an exploded perspective view of the prosthesis of FIG. 1.

FIGS. 1-3 illustrate an embodiment of an implantable prosthesis for repairing soft tissue or muscle defects. The prosthesis 20 includes an ingrowth layer 22 of tissue infiltratable material. The ingrowth layer 22 includes at least one layer of material that permits or is otherwise susceptible to tissue or muscle adhesions. In one embodiment the ingrowth layer includes first and second layers 22a, 22b joined together. Each layer 22a, 22b is formed of a biologically compatible, flexible material that includes a plurality of interstices or openings which allow sufficient tissue or muscle ingrowth to secure the prosthesis to host tissue or muscle after implantation.

In one embodiment, each layer 22a, 22b is formed of a knitted polypropylene monofilament mesh fabric, such as BARD MESH available from C.R. Bard, Inc. When implanted, the polypropylene mesh promotes rapid tissue or muscle ingrowth into and around the mesh structure. Alternatively, other materials which are suitable for tissue and muscle reinforcement and defect correction may be utilized, including SOFT TISSUE PATCH (microporous ePTFE—available from W.L. Gore & Associates, Inc.); SURGIPRO (available from US Surgical, Inc.); TRELEX (available from Meadox Medical); PROLENE and MERSILENE (available from Ethicon, Inc.); and other mesh materials (e.g., available from Atrium Medical Corporation). Absorbable materials, including polyglactin (VICRYL—available from Ethicon, Inc.) and polyglycolic acid (DEXON—available from US Surgical, Inc.), may be suitable for certain applications. Collagen materials, such as COLLAMEND from C.R. Bard, Inc. or SURGISIS available from Cook Biomedical, Inc., may also be used. It also is contemplated that the mesh fabric may be formed from multifilament yarns and that any suitable method, such as knitting, weaving, braiding, molding and the like, may be employed to form the prosthetic mesh material.

To ensure that adequate tissue or muscle ingrowth occurs, the two layers of material may be attached in a way that would permit tissue to grow into the interstices or pores of each layer 22a, 22b and provide a strong bond between the surrounding muscle or tissue and layer 22b. In one embodiment, the first and second layers 22a, 22b are connected with stitches 30.

In one embodiment, the first and second layers 22a and 22b are attached only at discrete locations. In this manner, tissue or muscle is able to grow through the first layer 22a and into the second layer 22b. Although a single stitch line 30 may adequately secure the ingrowth layers together, it may be desirable to use additional stitch lines to limit the amount of billowing of the ingrowth layers 22a and 22b. In addition, although the attachment is shown to include concentric patterns, any suitable pattern may be employed so as to minimize separation of the layers.

It should be appreciated that the invention is not limited to any particular attachment method, as the first and second layers may be attached using other suitable techniques. For example, the layers may be bonded together by melting the layers at specific locations or in a specified pattern; sonic, induction, vibration, or infrared/laser welding the layers; or using a suitable bonding agent. The point or points of attachment may comprise any suitable pattern, such as a spiral pattern, a serpentine pattern or a grid-like pattern of dots or beads, that maintains a sufficient quantity of open or non-impregnated interstices for tissue or muscle infiltration.

To aid in positioning and/or provisionally attaching the prosthesis, the prosthesis may include at least one pocket 32. In this manner, a surgeon may use the pocket to position the prosthesis in the desired area. Thereafter, the surgeon may suture or staple one of the layers of material to the surrounding ingrowth tissue, muscle or peritoneum layer. For example, the surgeon may enter the pocket and suture or staple the upper layer of the pocket to the tissue, muscle or peritoneum layer. As such, the prosthesis may be provisionally held in place at least until sufficient tissue or muscle ingrowth occurs. In one embodiment, the first and second layers 22a, 22b are attached in a manner to form the pocket 32 therebetween. However, it should be appreciated that the invention is not limited in this respect and that a pocket 32 need not be employed or that other suitable pockets formed in other suitable manners may be employed. For example, a pocket may be formed from an additional layer of material or portion thereof attached to the first layer 22a.

To gain access to the interior of the pocket, the prosthesis may include at least one opening to the pocket 32. In one embodiment, the opening includes an elongated cut or slit 34 formed in the first layer 22a. However, it is to be appreciated that the prosthesis may include any suitable opening that allows access to the pocket as would be apparent to one of skill in the art.

To position the prosthesis, the surgeon may insert one or more fingers (or a suitable surgical instrument) into the pocket and manipulate the prosthesis into place. In one embodiment, the pocket 32 is sized to accept several fingers of the surgeon's hand, although other suitably sized pockets may be employed, as the present invention is not limited in this respect. Further, the pocket 32 may be formed of multiple pockets with multiple openings so that one or more fingers may be inserted into individual finger sections.

In certain procedures, such as in the repair of ventral hernias or in the reconstruction of chest or abdominal walls, the ingrowth layer may come into contact with tissue, muscle or organs, which is not intended to grow into the ingrowth layer. Such contact could potentially lead to undesirable postoperative adhesions between the ingrowth layer and the surrounding tissue, muscle or organs. To minimize or eliminate the incidence of postoperative adhesions to selected portions of the prosthesis, the prosthesis may include a tissue, muscle or organ adhesion resistant barrier layer 36 overlying at least a portion, and preferably all, of one side of the ingrowth layer 22.

In one embodiment, the barrier layer 36 is attached to the prosthesis on the side adjacent to the second layer 22b. The prosthesis 20 may be positioned in a patient such that the barrier layer 36 faces the region of potential undesired adhesion, such as the abdominal viscera (e.g., intestines) or the thoracic viscera (e.g., heart or lungs). As will be discussed in more detail below, the barrier layer 36 is formed of a material and/or with a structure that does not substantially stimulate and in fact resists tissue, muscle or organ ingrowth and adhesion formation when implanted, thereby limiting or completely eliminating the incidence of undesired postoperative adhesions between the ingrowth layer and adjacent tissue, muscle or organs.

In one embodiment, the barrier layer 36 is formed from a sheet of expanded polytetrafluoroethylene (ePTFE) having fibril lengths—also referred to as pore size or internodal distance—that will not permit significant tissue ingrowth. In one embodiment, the fibril lengths of the ePTFE are less than 5 microns. In another embodiment, the fibril lengths of the ePTFE are less than 1 micron and in still another embodiment, the fibril lengths are less than 0.5 microns. Examples of other suitable materials for forming the barrier layer 36 include FLUORO-TEX Pericardial and Peritoneum Surgical Membrane and FLUORO-TEX Dura Substitute available from C. R. Bard, and PRECLUDE Pericardial Membrane, PRECLUDE Peritoneal Membrane and PRECLUDE Dura Substitute membrane available from W. L. Gore & Associates, Inc.

A representative and non-limiting sampling of other suitable micro to non-porous materials includes silicone elastomer, such as SILASTIC Rx Medical Grade Sheeting (Platinum Cured) distributed by Dow Corning Corporation, and microporous polypropylene sheeting (available from Celgard, Inc.) and film. Autogenous, heterogenous and xenogeneic tissue also are contemplated including, for example, pericardium and small intestine submucosa. Absorbable materials, such as SEPRAFILM available from Genzyme Corporation and oxidized, regenerated cellulose (Intercede (TC7)) may be employed for some applications. It is to be appreciated that other suitable biocompatible adhesion resistant materials also may be used.

The prosthesis 20 may be particularly useful in repairing tissue defects where conventional tissue approximation is not feasible, for example, the repair of a large defect, such as a large incisional hernia, particularly one which occurs in tissue or muscle weakened by previous surgery or in tissue or muscle of obese patients. For this purpose, the prosthesis 20 bridges the defect and supports the surrounding tissue or muscle as the tissue or muscle grows into the ingrowth layer and after such ingrowth occurs. In one embodiment, to support stresses induced by the patient (e.g., by patient movements), thereby limiting recurrent defects, it is desirable that the tissue or muscle be able to grow into the layer of ingrowth material that is best suited for supporting such stresses. Since the first layer 22a includes at least one opening 34, it is relatively less able to support the required stress. On the other hand, the second layer 22b includes no sizable openings, or other large discontinuities, and is generally uniform and is therefore more able to support the required load. Therefore, in the embodiment described herein, the load bearing layer is the second layer 22b.

It should be appreciated that the present invention is not limited in this respect and that the prosthesis 20 may be formed with suitably sized and shaped openings or discontinuities in the second layer 22b, provided such openings or discontinuities do not reduce the load bearing ability of the second layer beyond a tolerable amount. For example, a relatively smaller prosthesis may employ such openings or discontinuities. These openings or discontinuities may be used to help at least provisionally anchor the prosthesis and promote tissue ingrowth. Examples of prostheses employing such openings and discontinuities are described in U.S. Pat. Nos. 6,290,708 and 6,224,616, which are assigned to the assignee of the present invention and which are hereby incorporated by reference in their entireties.

To permit and facilitate tissue or muscle growth into the second layer 22b, the barrier layer 36 preferably may be attached to the second layer 22b in a way that permits tissue to grow into the pores of the second layer 22b and provide a strong bond between the surrounding muscle or tissue and the second layer 22b.

In one embodiment, the first and second layers 22a, 22b are attached together at discrete attachment lines, using stitches which allow sufficient tissue infiltration to the ingrowth layer, and in particular, the second layer 22b, while providing a connection between the first and second layers 22a and 22b. In addition, these same stitches (e.g., stitches 38) may be used to secure the second layer 22b to the barrier layer 36. Although stitch lines 38 may adequately secure the barrier layer 36 to the ingrowth layer 22, it may be desirable to use additional stitch lines, such as a center stitch line 39, to limit the amount of billowing of the barrier layer away from the ingrowth layer. Although the attachment is shown to include concentric patterns, any suitable pattern may be employed so as to minimize separation of the ingrowth layer and the barrier layer.

If desired, different sets of stitches may be used to secure the first and second layers 22a and 22b together as compared to stitches used to secure the second layer 22b to the barrier layer 36. For example, not all the stitch lines 30 are required to pass through the barrier layer 36. Rather, only the stitch lines 38 pass through the barrier layer 36. It is preferred that as few stitches as necessary are employed to secure the barrier layer 36 to the second layer 22b so that tissue or muscle adhesion on the barrier layer side of the prosthesis is minimized. Also, in the embodiment shown, the center stitch line 39 passes only through the second layer 22b and the barrier layer 36, as the first layer 22a includes the access opening 32 at that location.

Although, in one embodiment, the barrier layer 36 is attached to the ingrowth layer 22b with stitches, it should be appreciated that the invention is not limited in this respect, as the barrier layer may be attached using other suitable techniques. For example, the barrier layer may be bonded to the ingrowth layer by heating the layers, welding the layers, or using a suitable bonding agent. In either case, a suitable pattern, such as a spiral pattern, a serpentine pattern or a grid-like pattern of dots or beads may be used, provided a sufficient quantity of open or non-impregnated interstices is maintained in at least the second layer 22b for tissue or muscle infiltration.

When stitches are employed to attach the ingrowth layer 22b to the barrier layer 36, to further minimize adhesions, the stitches may be formed from a non-porous, adhesion resistant material. For example, the stitches may be formed with a suitable polytetrafluoroethylene (PTFE) monofilament. PTFE stitches may provide a softer, more flexible prosthesis that is easier to manipulate as compared to a prosthesis using other stitch materials, such as polypropylene monofilament. PTFE monofilament also facilitates the manufacturing process due to the low friction characteristics of the material. Nevertheless, it should be understood that any suitable material, such as polypropylene monofilament, may be employed for the stitches. For example, because some of the stitch lines do not pass through the barrier layer, or where no barrier layer is employed, materials other than an adhesion resistant material may be employed. For ease of manufacturing, however, all stitches may be formed of the same material, although the invention is not limited in this respect.

The layers may be stitched using a typical sewing stitch formed by a sewing machine using a bobbin and sewing thread. Preferably, the barrier layer is positioned on the ingrowth layer to face the sewing needle so that the locking portion of each stitch (i.e. the bobbin) is formed on the ingrowth side of the prosthesis rather than on the barrier side to reduce the incidence of localized adhesions with tissue, muscle or organs. The stitches may be formed using a #10 ball-tipped needle to reduce the potential incidence of ingrowth through the stitch holes. The sheets of ingrowth material with or without the barrier layer may be held by a frame during the sewing procedure on a computer controlled table that has been programmed with the desired stitch pattern.

While the barrier layer 36 preferably covers the entire surface of one side of the ingrowth layer 22, it is to be understood that the barrier layer 36 may be configured to cover only selected portions of one side of the prosthesis to enhance ingrowth from both sides in those portions free of the barrier layer. Similarly, the prosthesis may be configured such that the barrier layer covers the entire surface on one side of the prosthesis and covers one or more portions of the other side of the prosthesis.

In some instances, it may be desirable to isolate the outer peripheral edge of the prosthesis 20 from adjacent tissue, muscle or organs. In one embodiment, a peripheral barrier 40 extends completely about the outer peripheral edge 24 of the prosthesis 20 to inhibit adhesions thereto. It is to be understood, however, that the peripheral barrier 40 may be configured to cover only those selected portions of the outer peripheral edge of the prosthesis where protection from the formation of postoperative adhesions is desired.

The peripheral barrier 40 may be formed integrally with either the ingrowth layer 22 or the barrier layer 36. Alternatively, the peripheral barrier 40 may be formed by a separate component that is attached to or incorporated into the outer peripheral edge of the prosthesis. In one illustrative embodiment, the peripheral barrier 40 is formed from a portion of the ingrowth layer 22. In particular, the ingrowth layer 22 may be altered so as to substantially eliminate the tissue infiltratable interstices or openings along its outer margin, thereby creating a peripheral barrier 40.

In one embodiment, the peripheral edge 24 of layers 22 is melted to seal the material and form an outer peripheral barrier 40. The barrier layer 36 may be configured, such as with submicronal sized pores, so that a portion of the melted material of layer 22 becomes fused to the barrier layer 36. The peripheral edge 24 may be melted using any suitable process. In one embodiment, the peripheral edge 24 may be melted by heat sealing the layer. In the exemplary embodiment, the peripheral barrier 40 is formed by melting a ring of polypropylene mesh fabric to the ePTFE barrier layer 36 in a shape that approximates the desired configuration of the prosthesis. This may be accomplished by overlying oversized sheets of the mesh fabric and ePTFE material in a fixture and heat sealing the layers using a heated die configured with the desired shape of the prosthesis. The melted ring may be formed by applying heat to the fabric at a temperature range of approximately 320° F. to 400° F. for a period of approximately 3 to 5 seconds. The temperature chosen typically should be below the sintering temperature of the ePTFE barrier layer. Other sealing techniques may be used, such as ultrasonic, induction, vibration, infrared/laser welding and the like, as the present invention is not limited in this respect. Once fused, the ingrowth layer is stitched to the barrier layer, as described above, and subsequently die cut flush along a portion of the ring to complete the prosthesis with a peripheral barrier.

Other suitable techniques for creating a peripheral barrier may be employed, as the present invention is not limited in this respect. Examples of such other techniques are described in U.S. Pat. No. 7,404,819, which is assigned to the assignee of the present invention and which is hereby incorporated by reference in its entirety.

Although some embodiments described above include a barrier layer, the present invention is not limited in this respect. Thus, other embodiments may or may not include the barrier layer or the peripheral barrier.

In some instances, such as (but not limited to) the correction of relatively large defects, it may be desirable to employ a prosthesis that is sufficiently rigid so that it can be easily and effectively manipulated and positioned in the desired area yet sufficiently flexible so that the prosthesis is adequately tolerated by both the physician implanting the prosthesis and the patient receiving the prosthesis. The prosthesis should conform to the shape of the area being covered and should be sufficiently rigid such that the edges do not excessively curl. This attribute may be particularly useful with a large prosthesis sized for use with large defects in obese patients. Thus, according to one aspect of the invention, to balance the stiffness and flexibility, the prosthesis 20 includes a support assembly 50. The support assembly may be coupled to the ingrowth layer in any suitable manner.

The support assembly contributes to the stability of the prosthesis, allowing it to remain in a desired shape during the implantation procedure, subject to proper fixation techniques. This stability facilitates deployment and placement of the prosthesis by making it easy to handle. For example, the support assembly aids in allowing the prosthesis to remain substantially planar during implantation. During implantation of the prosthesis, sutures may be passed around the support assembly to maintain the prosthesis in generally the desired configuration and location.

In one embodiment, the stiffening member 51 is formed from a polydioxanone (PDO) monofilament having a diameter of approximately 0.038 inches. However, it is contemplated that the stiffening member may be formed of any biocompatible, resorbable or non-resorbable material, including monofilaments, multifilaments or molded shapes, provided suitable stiffness and handling properties are maintained. It should be appreciated that the stiffening member (or the individual filaments or bands collectively forming the stiffening member) may have any suitable cross-sectional size and shape, such as circular, square, rectangular, triangular, elliptical, etc.

In one embodiment, the stiffening member 51 is formed of a resorbable material. The resorbable stiffening member facilitates initial handling and deployment of the prosthesis. Thereafter, the stiffening member will gradually degrade until it is completely resorbed by the body. Such an arrangement may be advantageous in that the stiffening member is eventually resorbed by the body after it is no longer needed to facilitate the handling and deployment of the prosthesis.

In one embodiment, the stiffening member 51 is formed from a polydioxonane (PDO) monofilament having a diameter of approximately 0.038 inches. However, it is contemplated that the stiffening member may be formed of any biocompatible, resorbable or non-resorbable material, including monofilaments, multifilaments or molded shapes, provided suitable stiffness and handling properties are maintained. It should be appreciated that the stiffening member (or the individual filaments or bands collectively forming the stiffening member) may have any suitable cross-sectional size and shape, such as circular, square, rectangular, triangular, elliptical, etc.

In one illustrative embodiment, the prosthesis employs a stiffening member 51 that is configured in the shape of a ring. However, the stiffening member may be configured in any pattern, such as a spiral pattern, a square pattern, an elliptical pattern, a circular pattern or the like. In one embodiment as shown, the support assembly 50 employs a continuous, uninterrupted ring. The ring may be formed by joining the end portions of a length of material, such as a monofilament. However, it should be appreciated that the stiffening member may be formed of one or more discrete, discontinuous segments, arranged in any configuration that may impart suitable stiffness and handling to the prosthesis.

The sleeve 52 may be formed of a porous material that allows passage or infiltration of fluid and/or tissue to promote degradation and/or resorption of the stiffening member 51. In one embodiment, the material includes interstices or pores having a size from approximately 0.00035 in$^2$ to approximately 0.00085 in$^2$. It may be desirable to employ a sleeve having an interstice or pore size of approximately 0.00085 in$^2$ when the support assembly is used with an ingrowth layer 22 formed of material having a similar pore or interstice size of approximately 0.00085 in$^2$. A sleeve having a smaller interstice or pore size, such as approximately 0.00035 in$^2$, may be desired when the support assembly is used with an ingrowth layer 22 formed of material having a larger pore or interstice size, such as greater than 0.00085 in$^2$. However, it is to be understood that the sleeve may employ material having other suitable interstice or pore sizes as would be apparent to one of skill in the art.

In one embodiment, the sleeve 52 is formed from a mesh fabric that includes interstices or pores that allow tissue infiltration or ingrowth into the support assembly to eventually surround and resorb the stiffening member 51. In one embodiment, the sleeve is formed from a knitted polypropylene mesh. The mesh may be knitted with monofilament having a diameter of approximately 0.006 inches. The mesh may employ any suitable fabric pattern that provides desired properties. It is to be understood that the sleeve may be formed of any suitable mesh material including, but not limited to, the material used for the ingrowth layer or other biocompatible materials having suitable properties. It also is contemplated that the sleeve may be formed from multifilament yarns and that any suitable method, such as knitting, weaving, braiding, molding and the like, may be employed to form the sleeve.

In one illustrative embodiment shown in FIG. 3, the sleeve may be formed with two rings of mesh 52a, 52b that are attached to form the sleeve. Each mesh ring may have a width of approximately 0.25 to 0.38 inches. As shown, the stiffening member 51 is sandwiched between the mesh rings 52a, 52b which are attached to each along the inner and outer sides of the stiffening member to surround the stiffening member in a sleeve of material.

If desired, the sleeve may be configured as a unitary member that is formed with a single piece of material. In one illustrative embodiment shown in FIGS. 4-7, the support assembly 50 may employ a sleeve 52 configured as a tubular or sock-like member that receives the stiffening member 51 therein. In one embodiment, the sleeve is a tubular mesh fabric material.

Figure 4:
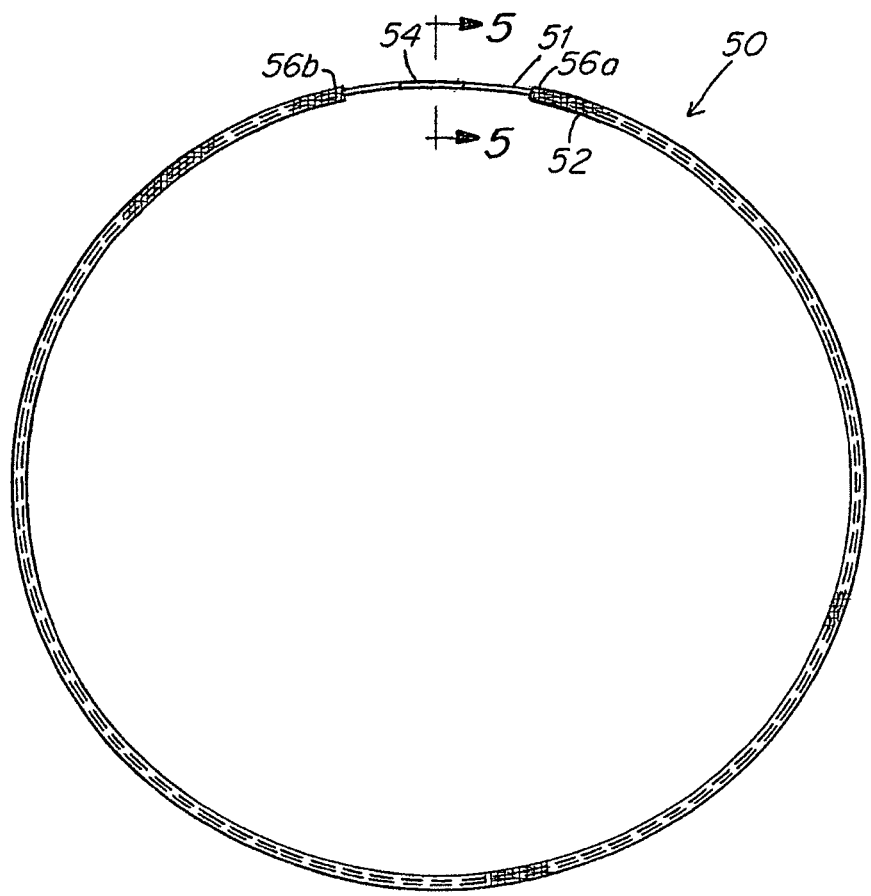
FIG. 4 is a top plan view of one illustrative embodiment of a support assembly for the prosthesis of FIG. 1 with the ends of a sleeve pulled back to join end portions of the stiffening member.
Figure 5:
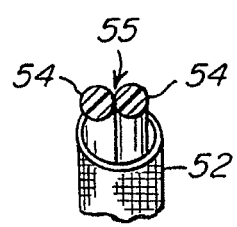
FIG. 5 is an enlarged cross-sectional view of the stiffening member taken along section line 5-5 of FIG. 4 illustrating the joint between the end portions of the stiffening member.
Figure 6:
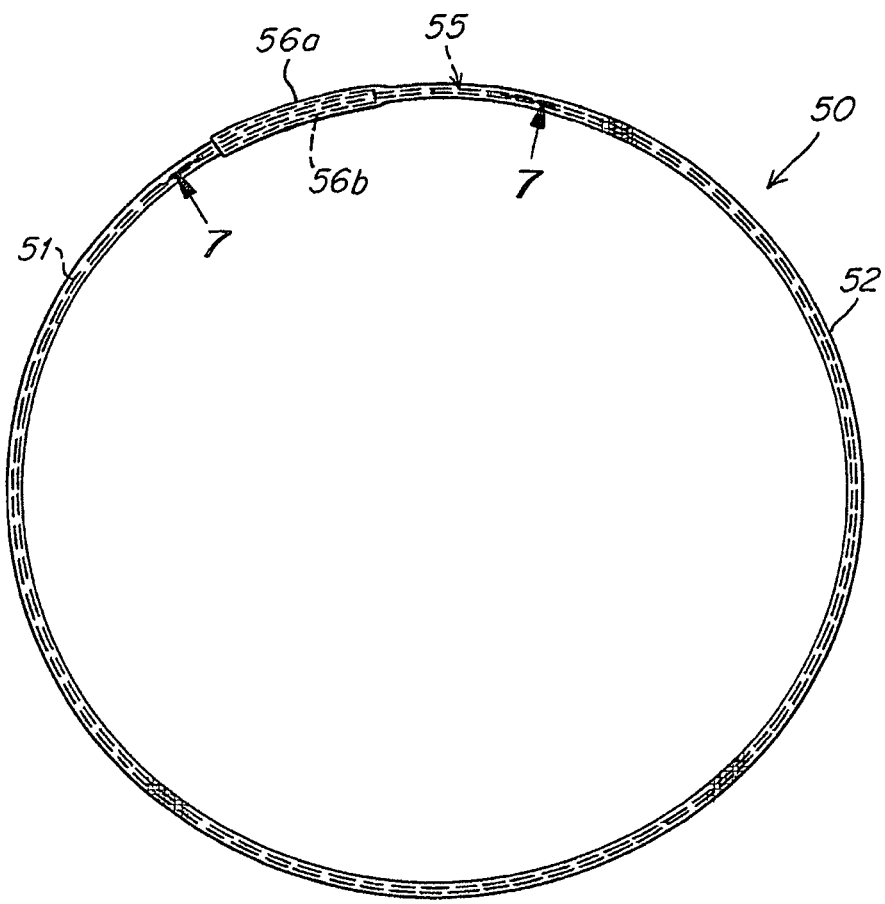
FIG. 6 is a top plan view of the support assembly of FIG. 4 with the stiffening member completely covered with a sleeve.
Figure 7:
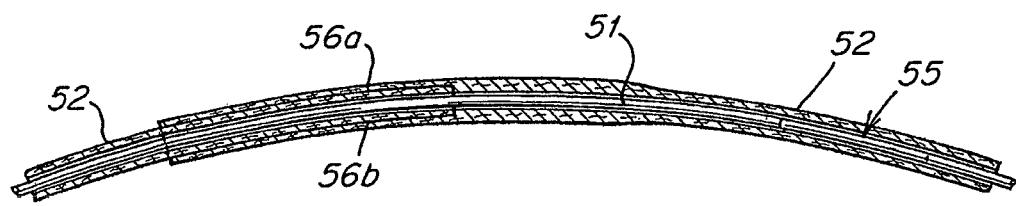
FIG. 7 is an enlarged cross-sectional view of the support assembly taken along section line 7-7 of FIG. 6.

As shown in FIG. 4, a length of material for the stiffening member 51 is inserted through the sleeve 52 and looped with the ends of the material being joined together to form a continuous ring configuration. As shown in FIG. 5, the end portions 54 of the stiffening member 51 may overlie and be joined together at a joint 55 using any suitable technique, such as welding, bonding and the like. After joining the ends 54 of the stiffening member, the ends 56a, 56b of the sleeve material are pulled together completely over the stiffening member 51 and joined to form a continuous sleeve over the stiffening member. As shown in FIGS. 6-7, the ends 56a, 56b of the sleeve 52 may overlap to completely cover the stiffening member. One end 56a of the sleeve material may be flared to fit over the opposite end 56b of the sleeve to ensure complete coverage of the stiffening member and facilitate joining of the sleeve ends.

Although several illustrative embodiments have been provided for the support assembly, it is to be understood that the support assembly may employ other structural arrangements apparent to one of skill in the art.

The support assembly 50 may be configured to surround the outer area 26 of the prosthesis and reinforce at least the outer area 26. In the embodiment shown in the figures, the support assembly 50 is not disposed at the peripheral edge 24. Rather, the support assembly 50 is spaced inwardly of the peripheral edge 24. However, it should be appreciated that the present invention is not limited in this respect, as the support assembly 50 may be disposed at the peripheral edge 24.

The support assembly 50 may be disposed on the prosthesis in any suitable manner as the present invention is not limited in this respect. In one embodiment, the support assembly 50 is sandwiched between the first and second layers 22a, 22b of ingrowth material and may or may not be physically attached thereto. A stitch line 30 formed by sewing threads may be stitched at least along or through the outside or inside edge 53a, 53b (FIG. 3) of the support assembly 50 to keep it from moving with respect to layers 22a and 22b. Because of the rigidity of the support assembly 50, one stitch line along or through one side of the support assembly 50 may be enough. However, preferably, two stitch lines, one on each edge of the assembly, secure the support assembly in place. Preferably, these stitches extend through both of the first and second layers 22a and 22b, but not through the barrier layer 36, if it is present. Another advantage is that the support assembly 50, if stitched or bonded to the barrier layer 36 or to the first and second layers 22a and 22b, holds the layers 22a, 22b and/or layer 36 together in a manner to prevent billowing of layer 36 with respect to layer 22 or layers 22a and 22b with respect to each other.

Alternatively, the support assembly 50 may overlie or underlie the ingrowth layer 22 and may be attached, regardless of location, with stitches or a bonding agent, or fused by ultrasonic, induction, vibration, infrared/laser welding and the like. In instances where a barrier layer is employed, it may be desirable that the support assembly 50 is not positioned under the barrier layer 36 or protrude therethrough, as doing so may result in undesirable adhesions forming on the support assembly.

Although the stiffening member 51 is described as being formed of a monofilament, it is to be understood that other suitable constructions may be employed. For example, the stiffening member may be one or more molded elements that are subsequently attached to, or molded onto, the prosthesis.

Figure 8:
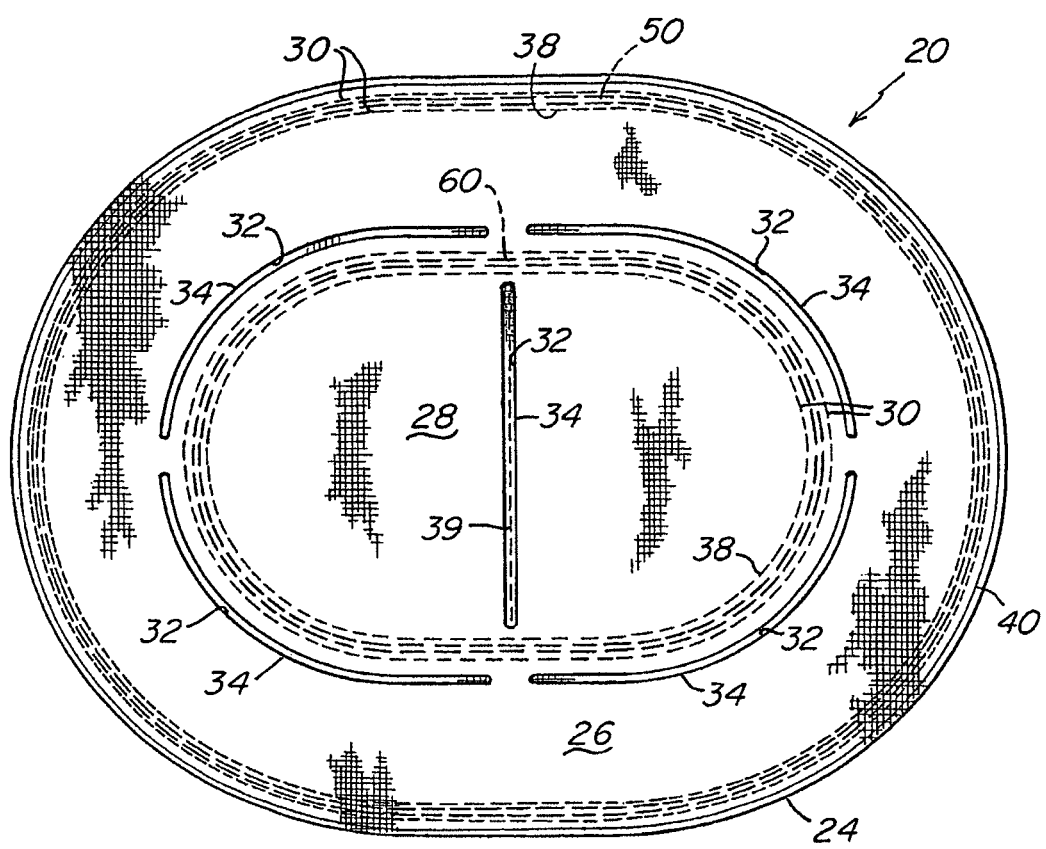
FIG. 8 is a top plan view of an implantable prosthesis employing multiple support assemblies according to another illustrative embodiment of the present invention.

In another embodiment shown in FIG. 8, a second support assembly 60 may be disposed inwardly of the first support assembly 50 and may be employed to reinforce the inner area 28 of the prosthesis. As shown, the second, inner support assembly 60 may be concentric or generally concentric with the first, outer support assembly 50. However, it should be appreciated that the invention is not limited in this respect as other suitable arrangements may be employed.

In one embodiment, the prosthesis 20 is relatively flat and sufficiently pliable to allow a surgeon to manipulate the prosthesis to insert the prosthesis and conform the prosthesis to the anatomical site of interest, allow the prosthesis to be sutured, stapled or otherwise anchored. The prosthesis 20 may be configured to have any suitable shape or size that is conducive to facilitating the correction of a particular defect. In the embodiments illustrated in the figures, the prosthesis 20 has a generally flat, oval shape. Examples of other shapes include, but are not limited to, circular, square, rectangular and irregular shapes.

In an exemplary embodiment, each of the first and second layers 22a and 22b is formed of an approximately 0.027 inch thick sheet of BARD MESH knitted from polypropylene monofilament with a diameter of approximately 0.006 inches. The barrier layer 36 is formed from an approximately 0.006 to 0.008 inch thick sheet of ePTFE. The barrier 36 is attached to layers 22a and 22b using approximately 3 mm to 4 mm long stitches formed of a 0.008 inch to 0.012 inch diameter PTFE monofilament.

In one embodiment, the prosthesis 20 has a generally oval shape that may have any desired size. For example, the prosthesis, as measured generally along the major and minor axes of the oval, may be approximately sized as follows: 5 inches by 7 inches; 7 inches by 9 inches; 8 inches by 10 inches; or 10 inches by 13 inches. The prosthesis may also be sized to cover an area greater than 50 square cm. In one embodiment, the prosthesis covers an area of approximately 68 square cm; in another embodiment, approximately 119 square cm; in yet another embodiment, approximately 152 square cm; and in still another embodiment, (e.g., for an obese patient) approximately 246 square cm. It should be understood, however, that the materials and dimensions described are merely exemplary and that any suitable sizes and shapes may be employed for the prosthesis.

In one embodiment, the prosthesis is sized such that the prosthesis overlaps the edges of the defect by at least 3 cm and, in some embodiments, by at least 4 cm and in still other embodiments, by at least 5 cm. Although the prosthesis has been described above as correcting a single defect, it is contemplated that a suitable sized and shaped prosthesis may be used to correct more than one defect.

Figures 9, 9A:
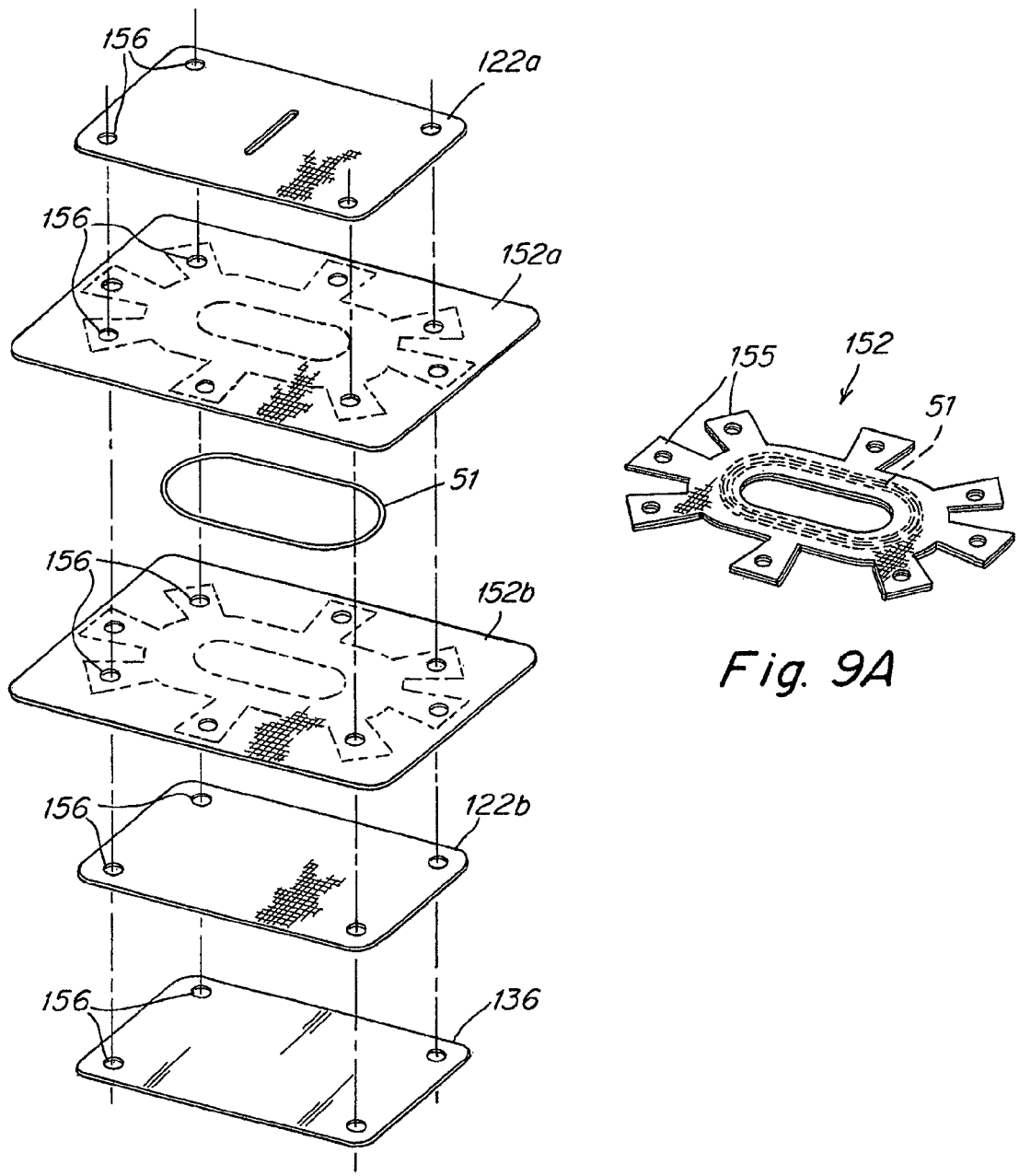
FIG. 9 is an exploded schematic view of a procedure for manufacturing the prosthesis of FIG. 1 according to one illustrative embodiment.
FIG. 9A is a schematic perspective view of the assembled support assembly of FIG. 9.

One example of a procedure to manufacture the prosthesis will now be described. The support assembly 50 is made by capturing the stiffening member 51 between two rings of die cut material 52a, 52b. FIG. 9 shows an exploded view of material blanks used to form the prosthesis 20. To form the support assembly 50, a mesh layer 152b is positioned flat on a multi-pin alignment fixture such that alignment pins pass through alignment holes 156 provided in each blank. Next, the stiffening member 51 is positioned on the mesh layer 152b. Thereafter, a mesh layer 152a is placed on top of the stiffening member 51, with the fixture alignment pins passing through corresponding alignment holes. A row of stitches is then placed on each side of the stiffening member 51 to attach the mesh layers 152a, 152b together and capture the stiffening member therebetween.

The assembled layers with the captured stiffening member are then die cut, to produce the support assembly 152 (as shown in FIG. 9A). As shown, the resulting assembly 152 includes a series of radially extending alignment tabs 155.

The support assembly 152 is positioned, using the alignment tabs 155, between the first and second layers 122a and 122b. The barrier layer 136 is positioned adjacent to the second layer 122b opposite the support assembly 152. The assembly is stitched together, using stitch patterns shown in FIGS. 1-2. The radial tabs 155 may then be removed and the assembly may be placed in a heated die to fuse portions of the first and second layers 122a, 122b to the barrier layer 136. A final die cut is then made to achieve the desired shape of prosthesis 20 with a resulting peripheral edge formed by the fused layers.

The illustrative procedure for manufacturing the prosthesis has been described in conjunction with using a support assembly 50 that is formed with multiple layers of material. As one of skill in the art would understand, a prosthesis using a support assembly that includes a tubular sleeve, as described above in connection with FIGS. 4-7, may be manufactured in a similar manner by positioning the tubular sleeve support assembly between the first and second layers 122a, 122b of material.

It should be understood that the foregoing description of various embodiments of the invention are intended merely to be illustrative thereof and that other embodiments, modifications, and equivalents of the invention are within the scope of the invention recited in the claims appended hereto. Further, the prosthesis described above includes various features that may be employed singularly or in any suitable combination.

What is claimed is:

1. An implantable prosthesis comprising:
a first layer of material having an outer periphery;
a second layer of material attached to the first layer, the second layer having an outer periphery; and
a support assembly located between the first and second layers of material and confined within the outer peripheries thereof, the support assembly including a stiffening member and a sleeve of material that separates the stiffening member from the first and second layers, the stiffening member located within and surrounded by the sleeve of material.

2. The implantable prosthesis of claim 1, wherein the first layer of material is configured to allow tissue ingrowth and the second layer of material is configured to inhibit the formation of adhesions thereto.

3. The implantable prosthesis of claim 1, wherein the stiffening member is formed of an absorbable material.

4. The implantable prosthesis of claim 3, wherein the stiffening member is formed of polydioxanone.

5. The implantable prosthesis of claim 3, wherein the sleeve is formed of an absorbable material.

6. The implantable prosthesis of claim 5, wherein the sleeve is formed of a material that is absorbable slower than the stiffening member.

7. The implantable prosthesis of claim 1, wherein the stiffening member includes a continuous ring.

8. The implantable prosthesis of claim 1, wherein the stiffening member is resilient.

9. The implantable prosthesis of claim 1, wherein the sleeve is configured to allow tissue ingrowth therethrough.

10. The implantable prosthesis of claim 9, wherein the sleeve is formed of a mesh fabric.

11. The implantable prosthesis of claim 1, wherein the sleeve is formed of a tubular fabric.

12. The implantable prosthesis of claim 1, further comprising a barrier layer that inhibits the formation of adhesions thereto, the barrier layer being attached to one of the first layer, the second layer and the support assembly.

13. The implantable prosthesis of claim 1, wherein at least one pocket is formed between the first and second layers.

14. The implantable prosthesis of claim 1, wherein the first and second layers are formed of mesh fabric.

15. The implantable prosthesis of claim 14, wherein the mesh fabric includes a knitted polypropylene mesh.

16. The implantable prosthesis of claim 1, wherein the first layer of material includes interstices having a first size and the sleeve includes interstices having a second size that is smaller than the first size.

17. An implantable prosthesis comprising:
a first layer of mesh having an outer periphery;
a second layer of mesh attached to the first layer of mesh with at least one pocket therebetween, the second layer of mesh having an outer periphery; and
a support assembly located between the first and second mesh layers, the support assembly including a stiffening member that is surrounded by material located between the stiffening member and the first and second layers of mesh, the support assembly confined within the outer peripheries of the first and second mesh layers.

18. The implantable prosthesis of claim 17, wherein the support assembly includes a sleeve of material that surrounds the stiffening member, the stiffening member being located in the sleeve.

19. The implantable prosthesis of claim 18, wherein the sleeve is configured to allow tissue ingrowth therein.

20. The implantable prosthesis of claim 19, wherein the sleeve includes a mesh fabric.

21. The implantable prosthesis of claim 20, wherein the sleeve is formed of a knitted polypropylene mesh.

22. The implantable prosthesis of claim 18, wherein the sleeve includes first and second rings of material that are joined together, the stiffening member being located between the first and second rings.

23. The implantable prosthesis of claim 18, wherein the sleeve includes a tubular fabric, the stiffening member being located within the tubular fabric.

24. The implantable prosthesis of claim 18, wherein the first layer of material includes interstices having a first size and the sleeve includes interstices having a second size that is smaller than the first size.

25. The implantable prosthesis of claim 18, wherein the sleeve is formed of an absorbable material.

26. The implantable prosthesis of claim 25, wherein the stiffening member is formed of an absorbable material and the sleeve is formed of a material that is absorbable slower than the stiffening member.

27. The implantable prosthesis of claim 17, wherein the stiffening member is formed of an absorbable material.

28. The implantable prosthesis of claim 27, wherein the stiffening member is formed of polydioxanone.

29. The implantable prosthesis of claim 17, wherein the stiffening member includes a continuous ring.

30. The implantable prosthesis of claim 17, wherein the stiffening member is resilient.

31. The implantable prosthesis of claim 17, further comprising a barrier layer that inhibits the formation of adhesions thereto, the barrier layer being attached to one of the first layer, the second layer and the support assembly.

32. The implantable prosthesis of claim 17, wherein the first layer includes an access opening to the at least one pocket.

33. An implantable prosthesis comprising:
a first layer of mesh fabric having an outer periphery;
a second layer of mesh fabric attached to the first layer of mesh fabric with at least one pocket therebetween, the second layer of mesh fabric having an outer periphery;
a support assembly located between the first and second layers of mesh fabric and confined within the outer peripheries thereof, the support assembly including an absorbable stiffening member surrounded with a sleeve of mesh fabric; and
a barrier layer that inhibits the formation of adhesions thereto, the barrier layer being attached to at least one of the first layer, the second layer and the support assembly.

34. The implantable prosthesis of claim 33, wherein the mesh fabric is configured to allow tissue ingrowth therein.

35. The implantable prosthesis of claim 34, wherein the mesh fabric includes a knitted polypropylene mesh.

36. The implantable prosthesis of claim 33, wherein the sleeve includes first and second rings of mesh fabric that are joined together, the stiffening member being located between the first and second rings.

37. The implantable prosthesis of claim 33, wherein the sleeve includes a tubular fabric, the stiffening member being located within the tubular fabric.

38. The implantable prosthesis of claim 33, wherein the stiffening member is formed of polydioxanone.

39. The implantable prosthesis of claim 33, wherein the stiffening member includes a continuous ring.

40. The implantable prosthesis of claim 33, wherein the stiffening member is resilient.

41. The implantable prosthesis of claim 33, wherein the first layer of material includes interstices having a first size and the sleeve includes interstices having a second size that is smaller than the first size.

42. The implantable prosthesis of claim 33, wherein the sleeve is formed of an absorbable material.

43. The implantable prosthesis of claim 42, wherein the sleeve is formed of a material that is absorbable slower than the stiffening member.

44. The implantable prosthesis of claim 33, wherein the first layer includes an access opening to the at least one pocket.

* * * * *